(12) United States Patent
Fan

(10) Patent No.: US 6,485,513 B1
(45) Date of Patent: Nov. 26, 2002

(54) PERCUTANEOUS STENT GRAFT AND METHOD FOR VASCULAR BYPASS

(75) Inventor: Chieh-Min Fan, Boston, MA (US)

(73) Assignee: The General Hospital Corporation, Boston, MA (US)

( * ) Notice: Subject to any disclaimer, the term of this patent is extended or adjusted under 35 U.S.C. 154(b) by 123 days.

(21) Appl. No.: 09/680,710

(22) Filed: Oct. 6, 2000

Related U.S. Application Data

(60) Provisional application No. 60/158,644, filed on Oct. 8, 1999.

(51) Int. Cl.⁷ ............................................. A61F 2/06
(52) U.S. Cl. .................... 623/1.36; 623/1.13; 623/1.23; 623/12; 606/153; 604/7; 604/8
(58) Field of Search ................ 600/36; 606/8, 606/151–156; 623/23.64, 23.7, 1.13, 1.14, 1.23, 1.36, 12; 604/7–8

(56) References Cited

U.S. PATENT DOCUMENTS

| | | | |
|---|---|---|---|
| 4,470,415 A | 9/1984 | Wozniak | 128/334 R |
| 4,787,386 A | 11/1988 | Walsh et al. | 128/334 R |
| 5,443,497 A | 8/1995 | Venbrux | 623/1 |
| 5,575,817 A | 11/1996 | Martin | 623/1 |
| 5,653,743 A | 8/1997 | Martin | 623/1 |
| 5,676,696 A | 10/1997 | Marcade | 623/1 |
| 5,676,697 A | 10/1997 | McDonald | 623/1 |
| 5,683,449 A | 11/1997 | Marcade | 623/1 |
| 5,709,713 A | 1/1998 | Evans et al. | 623/1 |
| 5,746,766 A | 5/1998 | Edoga | 606/198 |
| 5,755,775 A | 5/1998 | Trerotola et al. | 623/1 |
| 5,755,778 A | 5/1998 | Kleshinski | 623/1 |
| 5,776,185 A | 7/1998 | Verona et al. | 623/1 |
| 5,782,847 A | 7/1998 | Plaia et al. | 606/159 |
| 5,799,661 A | 9/1998 | Boyd et al. | 128/898 |
| 5,824,037 A | 10/1998 | Fogarty et al. | 623/1 |
| 5,824,040 A | 10/1998 | Cox et al. | 623/1 |
| 5,855,598 A | 1/1999 | Pinchuk | 623/1 |
| 5,860,998 A | 1/1999 | Robinson et al. | 606/194 |
| 5,861,026 A | 1/1999 | Harris et al. | 623/1 |
| 5,888,201 A | 3/1999 | Stinson et al. | 623/1 |
| 5,989,276 A * | 11/1999 | Houser et al. | 606/139 |
| 6,004,347 A | 12/1999 | McNamara et al. | 623/1 |
| 6,035,856 A * | 3/2000 | LaFontaine et al. | 128/898 |
| 6,036,702 A | 3/2000 | Bachinski et al. | 606/153 |
| 6,113,612 A | 9/2000 | Swanson et al. | 606/153 |
| 6,120,432 A * | 9/2000 | Sullivan et al. | 128/898 |
| 6,152,937 A | 11/2000 | Peterson et al. | 606/153 |

FOREIGN PATENT DOCUMENTS

| | | | |
|---|---|---|---|
| EP | 0 861 623 A2 | 9/1998 | A61F/2/06 |
| WO | WO96/41591 | 12/1996 | A61F/2/06 |
| WO | WO98/27893 | 7/1998 | A61F/2/06 |
| WO | WO98/32399 | 7/1998 | A61F/2/06 |

* cited by examiner

*Primary Examiner*—David J. Isabella
*Assistant Examiner*—Urmi Chattopadhyay
(74) *Attorney, Agent, or Firm*—Nutter McClennen & Fish LLP

(57) ABSTRACT

A prosthetic vessel graft assembly has a tube of synthetic graft material surrounding a stent at its distal end, together with a plurality of collapsible anchors projecting radially from the stent. The assembly mounts on an introducer that may be tunneled through skin or inserted in an opening and pushed down to a vessel for introducing the graft through the vessel side wall. The introducer is configured to follow a guide wire which is inserted via a needle through an opening in the side wall of the vessel. A peel-away sheath covers the stent, graft, and anchor members at the distal end keeping them collapsed against the tubular body.

6 Claims, 6 Drawing Sheets

PERCUTANEOUS STENT GRAFT AND METHOD FOR VASCULAR BYPASS

CROSS-REFERENCE TO RELATED APPLICATIONS

This application is related to and claims the benefit under 35 USC 119(e) of United States Provisional Application Ser. No. 60/158,644 filed by the inventor on Oct. 8, 1999.

STATEMENT REGARDING FEDERALLY SPONSORED RESEARCH

Not Applicable.

BACKGROUND OF THE INVENTION

The present invention relates to methods and procedures for accessing and forming a bypass in a vessel or between vessels.

There are a great number of circulatory conditions requiring surgical intervention to place a graft either as a complete substitute for a dysfunctional vessel, a bypass about a stenotic portion of a vessel, or a replacement for a surgically removed portion of the vessel. For the most part, such vascular grafts are placed surgically, entailing surgical exposure of the native vessel at the junction sites, surgical arteriotomy or venotomy to open the vessel, and suturing of the graft material to the vessel or to tissue served by the vessel. A great number of prosthetic grafts have been developed to address problems such as the apportionment of flow at branching junctions, the matching of vessels of different sizes when such junction is necessary, and the fitting of vessels to a region of tissue such as the wall of a cardiac chamber, so as to establish a more or less natural blood flow.

In addition, recently a number of approaches have been proposed or developed for forming a junction with a natural vessel, or a bypass between points of one or more vessels, by percutaneous or interstitial access. For example, U.S. Pat. No. 5,443,497 of Venbrux and U.S. Pat. No. 5,755,775 of Trerotola et al. illustrate such devices wherein an acutely angled Y-junction or an expandable stent junction is inserted at a low angle to the side of a vessel and secured to form a connecting port or conduit. Percutaneous access and installation are effected, for example, by using a peel-away sheath to release the penetrating junction member, in a manner similar to that of various tunneling trocar placement procedures conventionally used for routing prosthetic vessels through muscle tissue. However, these approaches essentially create Y-junctions, using a structure analogous to a in-vessel stent to effect a seal along the remaining open portion of the vessel. This access geometry with a low angle of entry necessarily entails a long incision in the vessel side wall and requires an oblique and possibly traumatic access route through surrounding tissue for installation along a smoothly contoured path. The Y-geometry entrance may further partially obstruct a vessel or divert flow in an irregular or inappropriate manner.

Accordingly, it would be desirable to provide a method and system for percutaneous access to a blood vessel for establishing a graft bypass or shunt with the vessel.

It would further be desirable to provide such a system adaptable to diverse geometry, or adaptable to arterial bypass, arterial to veinous grafts for dialysis access, and veinous to veinous grafts for occlusions or stenosis.

It would also be desirable to provide such a system forming a true end-to-side anastomosis.

SUMMARY OF THE INVENTION

One or more of these desirable objects are achieved in accordance with the present invention by a prosthetic vessel graft having a tube of synthetic graft material surrounding a self expanding stent. The graft and stent are mounted on a stiff introducer member which may be tunneled through skin or inserted in an opening and pushed down to a vessel for introducing the graft through the side wall of a vessel. Preferably the introducer has a hollow core and is configured to follow a guide wire which may be initially inserted by conventional techniques up to and through an opening in the side wall of the vessel. A peel-away sheath covers the stent and graft, and the stent has a plurality of collapsible anchor members at its distal end in the form of wire-like arms or hooks which initially are held tightly against the circumference of the stent and which spring outwardly in a radial direction when released from the sheath. In use, the intravascular end of the graft is inserted through an opening in the side of the vessel and the sheath is removed to release the anchors and secure the graft as a pure end-to-side anastomosis to the vessel.

In a preferred practice of the invention, a basic graft unit consists of the prosthesis tube and anchoring stent within the tube at one end thereof. The other (extravascular) end of the graft tube may have a blood compatible fitting or connector, or may have a reinforced band or collar suitable for suturing or other surgical joining technique. Two such prostheses are employed in a bypass procedure, and one is installed as described above at each vessel access point of an intended shunt or bypass. The two extravascular ends and bodies of the respective prostheses are then tunneled through tissue to a common point at a proximal cut-down or opening. Each segment is then back-flushed with saline and the ends are joined to each other, by suturing or by a quick-connect fitting that is attached or preattached to each of the prostheses, thus connecting them into a single continuous bypass or shunt. The opening may then be closed.

BRIEF DESCRIPTION OF THE DRAWINGS

These and other features of the invention will be understood from the discussion below taken together with the drawings and claims herein, wherein:

DETAILED DESCRIPTION

Figure 1:
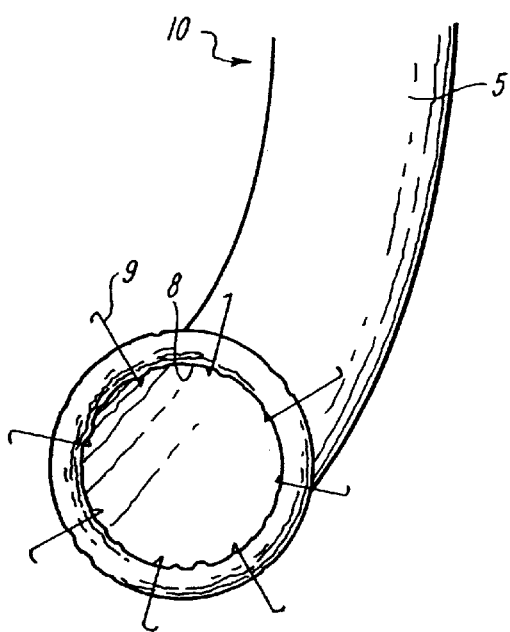
FIG. 1 shows a distal end view of one embodiment of a prosthetic graft in accordance with the present invention.

FIG. 1 shows an end view of a graft in accordance with the present invention. As illustrated the graft 10 has a generally tubular form with an outer layer or skin 5 formed of a synthetic polymer of a type conventionally used or suitable for a vessel prosthesis, and an inner stent structure 8 at the distal end that provides shape and support for the layer 5. The layer 5 may be made of knitted or woven dacron, porous expanded PTFE, various hybrid constructions or other suitable prosthesis material. The inner stent structure 8 includes a generally annular circumferential support band and further includes a number of radially projecting arms or anchor hooks 9 extending therefrom. The anchor hooks or arms 9 are illustrated as bare wires, but in practice applicant contemplates that they may be coated, or preferably are covered by a membrane (e.g., the PTFE "onionskin" membrane commonly used as a wrap or reinforcement, and/or by other material similar to layer 5 or having some porosity, compliance or suitable mechanical or biological properties) to provide continuity with the main tubular layers of the graft as well a certain amount of tissue compatibility and sealing, as described further below. In addition to the stent and anchoring structures 8, 9 at the distal end of the graft, the same stent structure, or one or more separate and additional stents or stent rings, may extend to or be placed along the intermediate or proximal length of the graft to maintain its shape.

Figure 2:
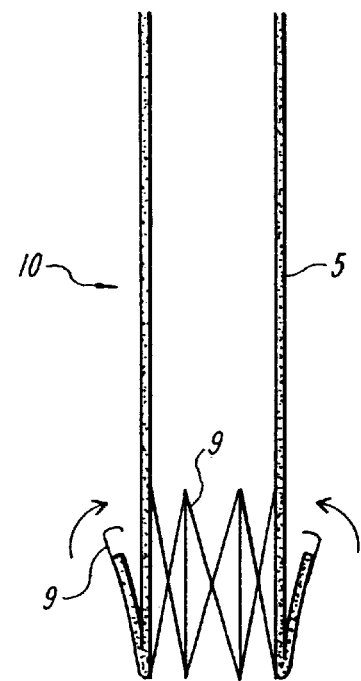
FIG. 2 shows a side view thereof before deployment.
Figure 3:
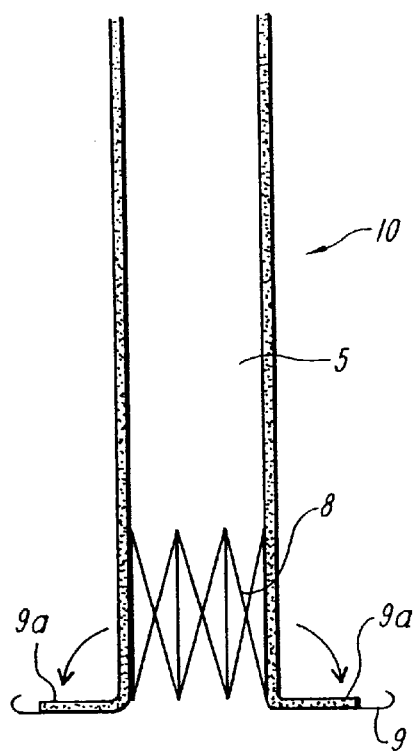
FIG. 3 shows a side view thereof after deployment.

FIG. 2 illustrates the graft 10 of FIG. 1 in a side view, showing the arms 9 collapsed inwardly against the cylindrical body of the graft. As discussed further below, this is the normal orientation of the arms for shipping, handling and initial installation. FIG. 3 shows the stent with the arms 9 in an outward or extended position. This sagital cross section further illustrates the preferred construction, with one or more membranes 9a forming an umbrella-like seal of skin continuous with the graft wall 5 and positioned to extend as a prosthesis flange covering a band against the vessel wall surrounding the point of vessel penetration.

Figure 4:
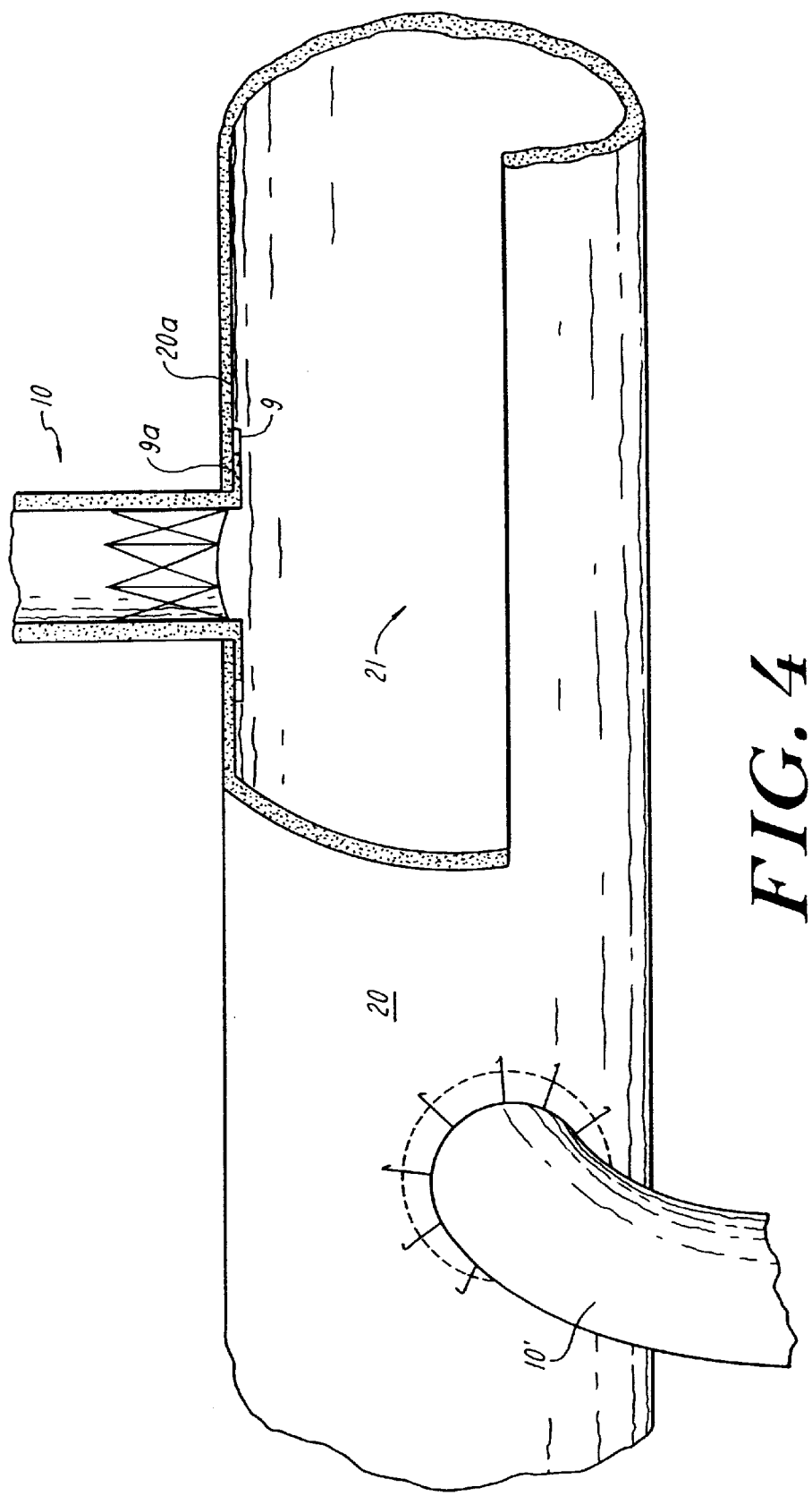
FIG. 4 shows a schematic and partially cut-away view of the graft connected to a vessel.

In use, the method of the present invention proceeds by inserting graft 10 through an opening in the side wall of a natural vessel 20 (FIG. 4) to form a true end-to-side anastomosis therewith. As shown in FIG. 4, when installed in this fashion, the anchor hooks 9 and membrane 9a reside inside of the vessel 20 and bear against the inner wall 20a of the vessel, thus preventing dislodgement of the graft 10 from the vessel. FIG. 4 further shows a second graft 10' in a perspective view from outside the vessel. As shown, the grafts 10, 10' join the vessel at substantially normal incidence. Further, as seen in the partial cut away view, within the vessel the graft ending lies closely against and fastens tangent to the endoluminal surface of the vessel wall without projecting into the blood flow lumen 21.

Figure 5:
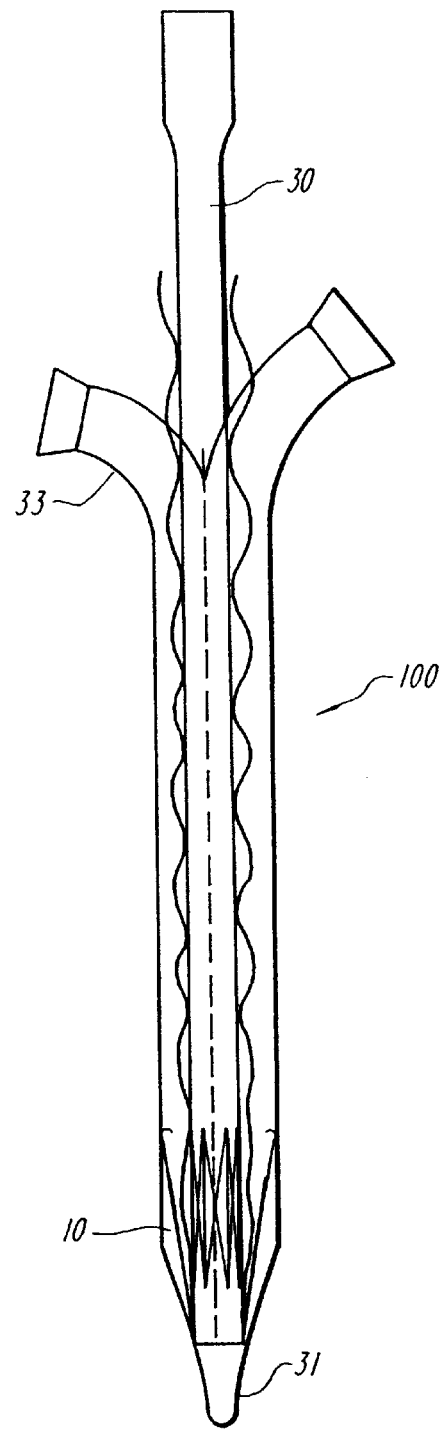
FIG. 5 shows a delivery system and graft of the invention.

The stent 10 is delivered by a delivery system 100 in accordance with a method of the present invention as shown in FIG. 5. Generally the stent is collapsed as shown in FIG. 2 for delivery to the vessel site and deployment through the vessel wall. The stent is placed onto a stiff but preferably flexible introducer 30 having a trocar-like penetration end 31 with a shape capable of enlarging and entering an opening in the wall of the vessel, and the graft assembly is covered with a peel-away sheath 33 which maintains the anchor arms 9 retracted flat against the stent wall. The sheath 33 also provides a smooth, frictionless and nonabrading surface along the outside of the assembly for atraumatic introduction through tissue or along an incision to the vessel entry site. The introducer 30 is sufficiently stiff to transfer axially-directed pushing force and to allow steering manipulation of the device. It may also have a central guide wire lumen to allow it to initially position, or to subsequently follow, a guide wire.

Generally, applicant contemplates that for deployment of the stent assembly to a vessel, for example to a femoral, popliteal or axillary artery for creating a connection or shunt, and to a vein for creating an A V dialysis graft or a veinous bypass, the precise site of placement will be accessed by a method similar to existing angiographic catheter and wire introduction techniques. This may be a modified Seldinger technique, involving a cut down to or accessing of the vessel with a needle (not shown) and guide wire 35. Once the guide wire has been placed within the vessel, the introducer may be placed over and follow the guide wire to the entry point and dilate it to admit the end of the stent graft introducer 30, positioning the distal end of the stent graft within the vessel. The procedure may be visualized fluoroscopically to assure that the distal graft end and arms 9 have passed beyond the puncture site and are sufficiently within the vessel. The proximal end of the graft is then clamped to control blood loss, the introducer 30 is removed and the peel-away sheath 33 is removed under fluoroscopic observation to release the anchor hooks 9 from their constrained position so that they open outwardly and assume a radial disposition.

Preferably, the distal stent and anchor assembly is formed of a shape memory alloy which self-deploys. In particular, the arms 9 change to a hook-anchor radially-extending orientation when released by removal of the sheath. The annular support portion of the stent 8 may also be configured to self-deploy upon release such that it assumes a larger diameter, or so that it exerts an outward resilient force in the tubular neck region at the vessel entry. After removal of the sheath 33, the graft is then pulled back to engage the hooks against the inner vessel wall and seal the graft assembly tightly against the inner wall of the vessel in the region surrounding the graft entry site. The exterior surface of the graft in the distal region may be coated with suitable growth enhancers, surgical tissue glue, or other biocompatible or bioactive material, as appropriate to enhance tissue sealing.

For forming a bypass or shunt, a similar or identical stent graft is attached to another vessel or another point on the same vessel, depending upon the desired type of graft, and once both anastomoses are anchored at their respective vessel entry points, the stent grafts are tunneled subcutaneously and externalized through a single skin incision. This tunneling procedure is similar to that used in interventional radiology for installing veinous access devices. The externalized ends of the stented grafts are then back-bled to flush out accumulated clot material, and are joined to form a single vessel-to-vessel graft. They may be end-to-end anastomosed with sutures, or connected with a mechanical connector device such as a suitable snap-ring, quick-connect, or other mechanical vessel connector assembly. The completed bypass is then dropped back into the tunnel and the skin incision is closed.

Figure 6B:
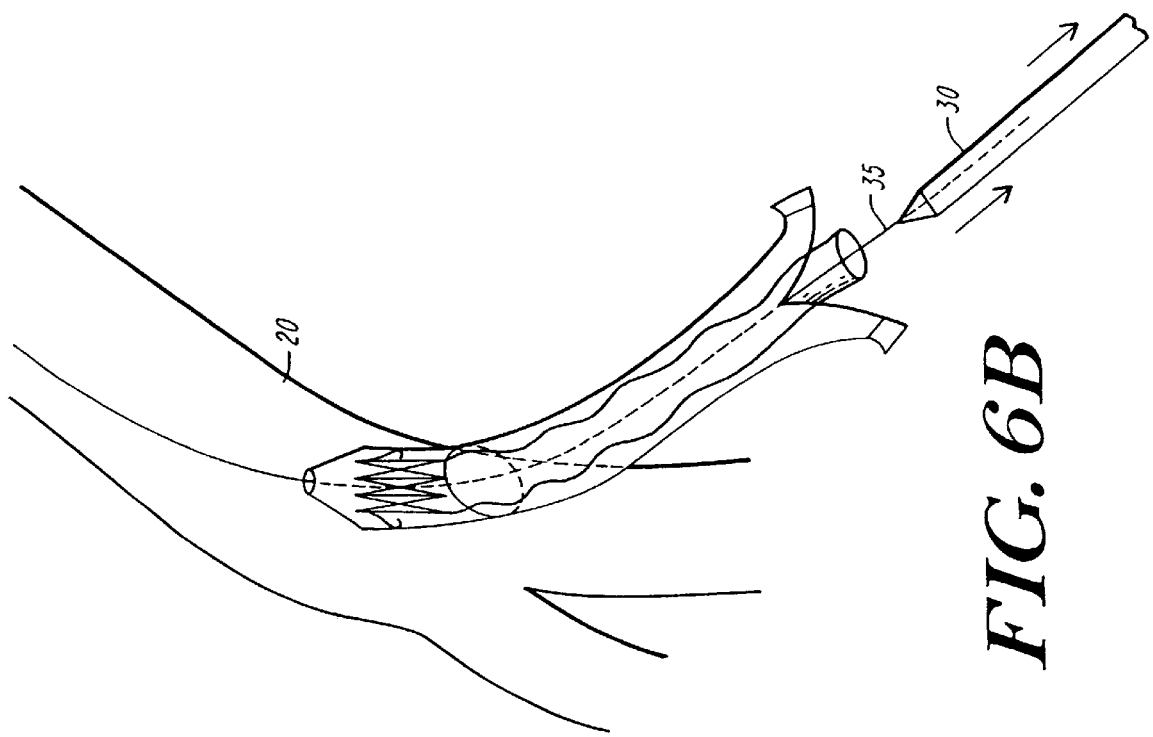
FIGS. 6A–6D illustrate the method of deployment.
Figure 6A:
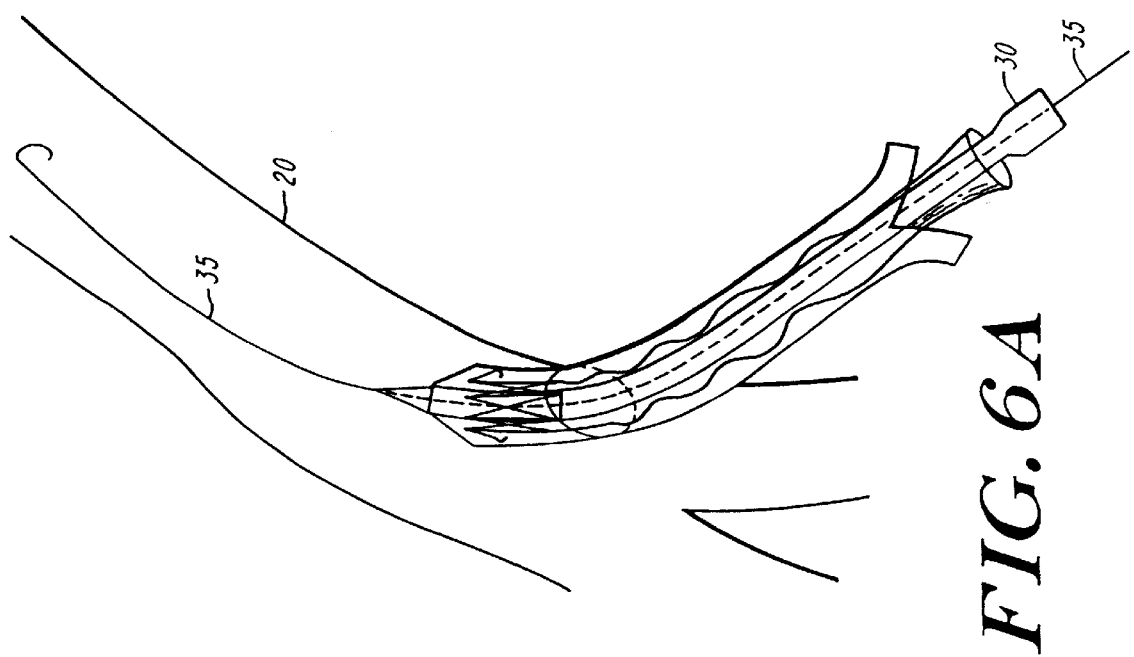
Figure 6D:
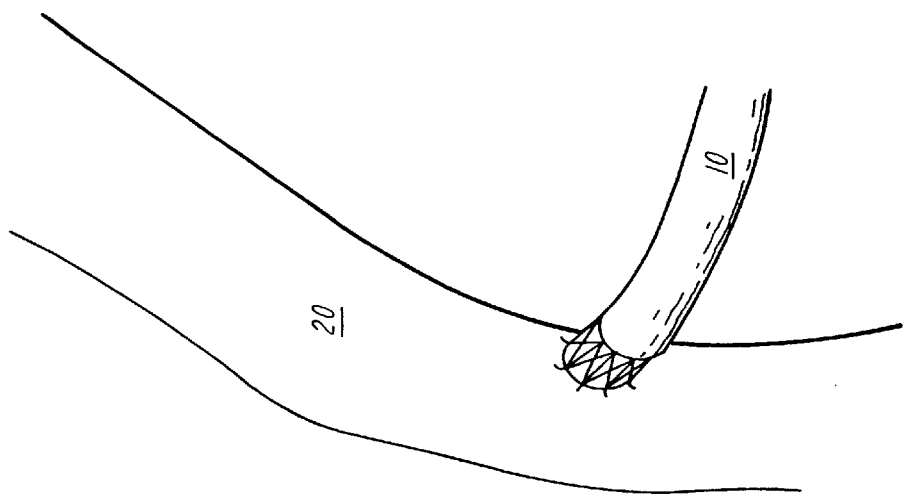
Figure 6C:
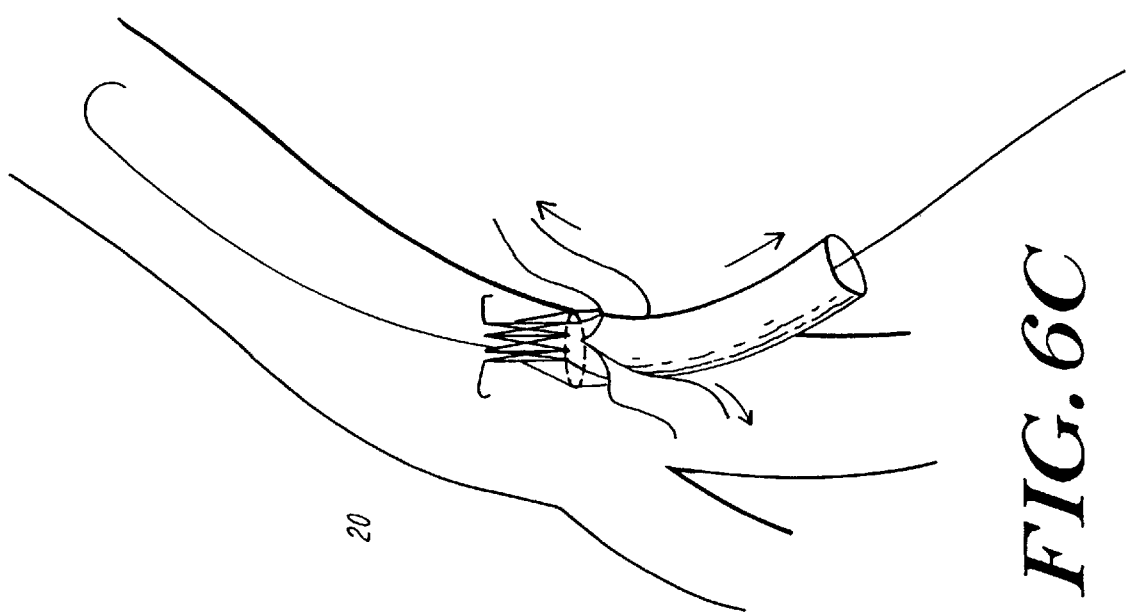
Figures 7A, 7B:
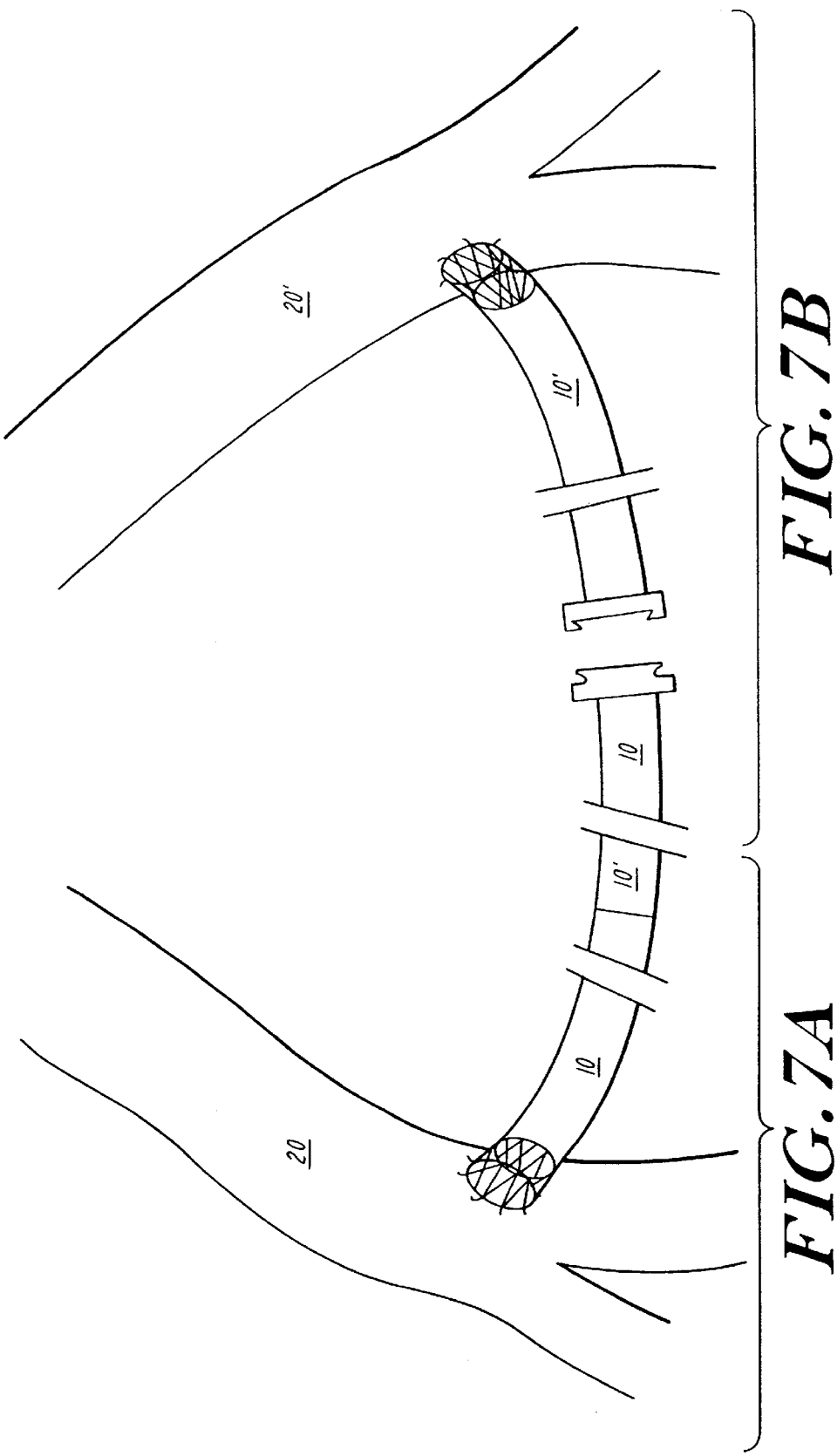
FIGS. 7A–7B illustrate further steps in forming a shunt or port utilizing plural grafts of the invention.

FIGS. 6A through 6C illustrate such guide wire introduction of the graft to the vessel, and show the removal of the introducer and release of the anchor arms. FIG. 6D shows the completed end-to-side anastomosis. FIGS. 7A and 7B illustrate the connection of two stented grafts via a sutured or mechanical snap ring connection to form a bypass or shunt as described above.

This completes a basic description of one implementation of a percutaneous stent graft and method of forming vessel-to-vessel grafts in accordance with the present invention. The invention being thus disclosed, variations and modifications will occur to those skilled in the art, and all such variations and modifications are considered to be within the scope of the invention, as defined by the claims appended hereto and equivalents thereof.

What is claimed is:

1. A prosthetic vessel comprising a generally tubular prosthesis formed of biocompatible synthetic material a stent carried within a distal end of said tubular prosthesis, said stent including a first section arranged generally coaxial with said tubular prosthesis, and an anchor portion comprising a plurality of gripping elements extending from the stent, the gripping elements being configured to self-deploy from a constrained position, in which the gripping elements are positioned in a substantially flat orientation against an outer wall of the prosthesis, to an open position upon deployment in which the gripping elements extend radially from said tubular prothesis for securing the end of the graft to a vessel in an end-to-side anastomosis when inserted through an opening in the vessel side wall, and a selectively removable peel-away sheath formed over the outer wall of the prosthesis, effective to maintain the gripping elements in the constrained position.

2. The prosthetic vessel of claim 1, wherein said gripping elements are integral with said stent.

3. The prosthetic vessel of claim 2, wherein said gripping elements are formed of shape memory alloy.

4. The prosthetic vessel of claim 3, wherein said stent is formed of shape memory alloy.

5. The prosthetic vessel of claim 1, wherein said stent and gripping elements are positioned at a distal end of the generally tubular prosthesis to form a self-anchoring inner flange for end-to-side anastomosis of the prosthetic vessel.

6. The prosthetic vessel of claim 5, further comprising one or more stents located in a proximal portion of said generally tubular prosthesis.

* * * * *